United States Patent [19]
Scordato et al.

[11] 4,371,498
[45] Feb. 1, 1983

[54] CODED CUVETTE FOR USE IN TESTING APPARATUS

[75] Inventors: Richard E. Scordato, Scarsdale, N.Y.; Robert J. Varca, Fort Lee, N.J.

[73] Assignee: Medical Laboratory Automation, Inc., Mount Vernon, N.Y.

[21] Appl. No.: 275,419

[22] Filed: Jun. 19, 1981

[51] Int. Cl.³ .......................... G01N 35/00; B01L 3/00
[52] U.S. Cl. .................................. 422/102; 356/246; 422/67
[58] Field of Search ................. 422/61, 65, 67, 102; 356/246

[56] References Cited

U.S. PATENT DOCUMENTS

| | | | |
|---|---|---|---|
| 3,718,439 | 2/1973 | Rosse et al. | 422/67 |
| 3,994,594 | 11/1976 | Sandrock | 422/102 |
| 4,013,368 | 3/1977 | Acker | 356/246 |
| 4,119,407 | 10/1978 | Goldstein et al. | 422/101 |
| 4,195,059 | 3/1980 | Whitcher | 422/61 |
| 4,207,289 | 6/1980 | Weiss | 422/65 |
| 4,249,826 | 2/1981 | Studievic | 356/246 |
| 4,251,159 | 2/1981 | White | 356/246 |

*Primary Examiner*—Michael S. Marcus
*Attorney, Agent, or Firm*—William P. Keegan

[57] ABSTRACT

A dual receptacle cuvette adapted for use in a plasma coagulation testing apparatus which cuvette is coded to enable the apparatus to determine the particular test procedure to be performed on the plasma sample in the cuvette receptacles.

7 Claims, 5 Drawing Figures

CODED CUVETTE FOR USE IN TESTING APPARATUS

BACKGROUND OF THE INVENTION

Containers of many different types and shapes have been provided for specimens or patient samples that are later mixed with reagents and analyzed to give an indication of a property or condition of the test sample. For example, U.S. Pat. No. 3,905,772 discloses a multi-unit cuvette that is useful in analyzing the blood group of a plasma sample. U.S. Pat. No. 3,607,099 discloses a coagulation apparatus which determines the prothrombin time of a plasma sample placed in a single cuvette to which a reagent is added. U.S. Pat. No. 3,969,079 discloses a cuvette disk having a plurality of sample receptacles arranged in concentric rows. Two receptacles, one from each row, will be radially aligned so that two samples may be analyzed simultaneously. For example, a prothrombin time measurement may be made on each sample, or an activated partial thromboplastin measurement may be made on each sample, or a prothrombin time measurement may be made on one sample while an activated partial thromboplastin measurement may be made on the other sample.

SUMMARY OF THE INVENTION

The present invention is directed to a multi-receptacle unitary cuvette that is especially adapted for use in an apparatus capable of determining, for example, either prothrombin time or the activated partial thromboplastin time of a plasma sample. The apparatus may measure other blood related factors. More particulary, the invention is directed to a multi-receptacle cuvette which is coded to be machine readable so as to enable an appropriate apparatus to perform one analysis or another on the sample contained in the receptacles. The same analysis or test may be made on the samples in each receptacle, and, if the samples are from the same patient, the test results may be averaged to provide a more accurate determination of the measured factor. Or a different analysis may be made on each sample in each receptacle of the cuvette. The analysis performed will be determined by the cuvette coding.

Thus, the object of the invention is to provide an improved cuvette for use in a coagulation apparatus.

Another object of the invention is to provide a coded cuvette that informs the coagulation apparatus of the type test that is to be performed on the sample therein.

Still another object of the invention is to provide a multi-receptacle coded cuvette so that a plurality of tests may be performed sequentially on the samples in each receptacle.

In carrying out the invention, a multi-receptacle cuvette is provided having two receptacle members separated by a central connecting member that joins the receptacle members to form a unitary cuvette. The upper portion of a sidewall of the cuvette is provided with one or more apertures to form a machine readable code that determines the test or tests that will be performed on the fluid samples in the receptacles. The central connecting member of the cuvette is configured to enable it to be engaged by a movable member of the testing apparatus so that the cuvette is secured in an aligned position in the apparatus.

Features and advantages of the invention may be gained from the foregoing and from the description of a preferred embodiment of the invention which follows.

DETAILED DESCRIPTION OF THE INVENTION

Figure 1:
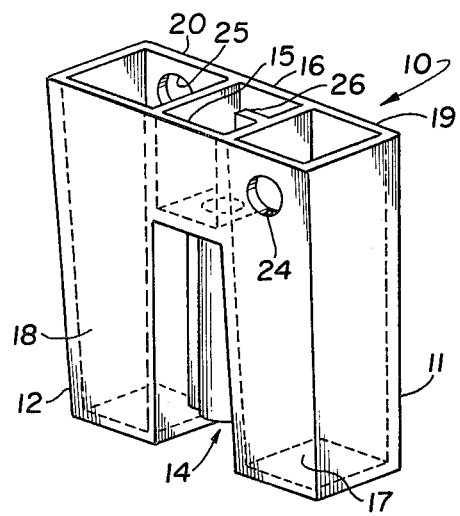
FIG. 1 is an isometric view of the cuvette of the present invention.
Figure 2:
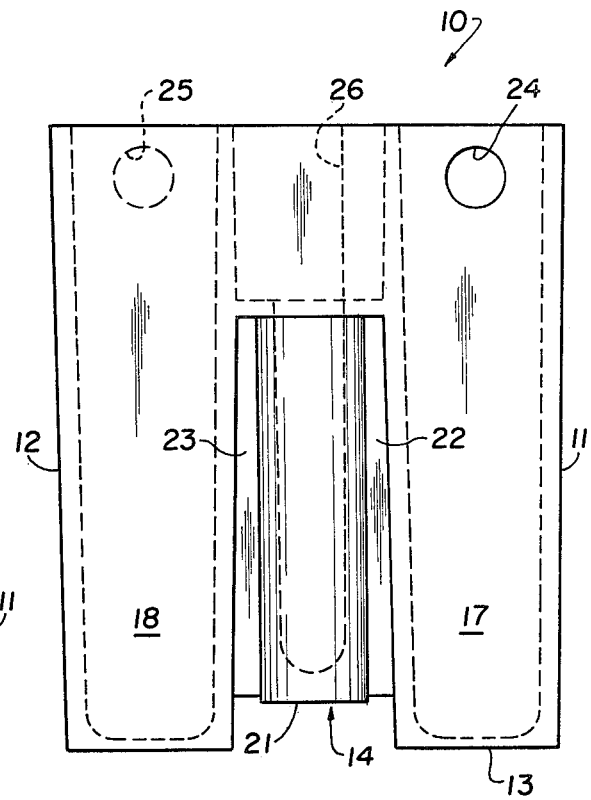
FIG. 2 is a front elevational view of the cuvette.
Figure 3:
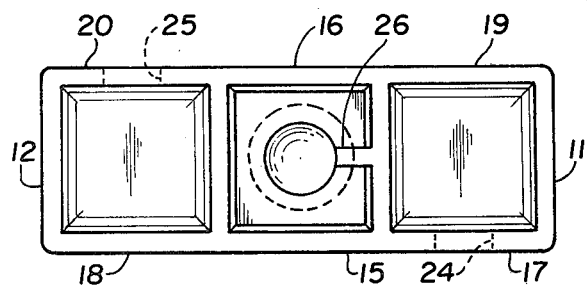
FIG. 3 is a top plan view of the cuvette.
Figure 4:
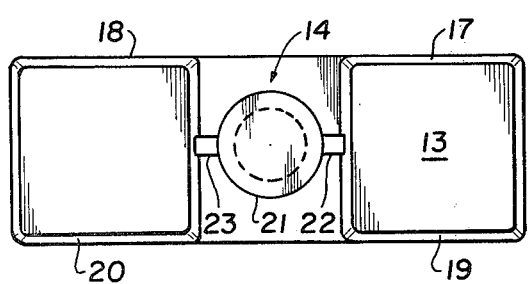
FIG. 4 is a bottom plan view of the cuvette.

Referring to the drawing in general, the cuvette 10 is seen to comprise a first sample receptacle 11 and a second sample receptacle 12. Each receptacle preferably has planar walls so as to minimize distortion when the receptacle is placed in a photo-optical clot detection apparatus and a beam of light is projected through a plasma-reagent mixture therein. Moreover, the bottom wall 13 of each receptacle is made flat and as thin as practicable so as to enhance heat transfer from and to a fluid sample placed in the receptacle. For example, a plasma sample, before being tested and while in the test apparatus will be maintained at a temperature of about 8° C. to prevent deterioration of the plasma. When the clotting or other properties of the plasma are being tested, the plasma temperature will be raised to the normal blood temperature of 37° C. The present cuvette is adapted to have the cooling and heating of a plasma sample therein effected through the bottom wall of the cuvette as it is moved along a cooled or heated track in the testing apparatus.

It will also be noted that the depth of a receptacle is several times the width of the receptacle. In an actual embodiment of the invention, the width of the receptacle is about $\frac{1}{4}''$ square and the depth over $\frac{3}{4}''$. With the volume of plasma and reagents presently used in coagulation tests, the test mixture will rise to a conveniently measurable height of liquid in the cuvette.

The two receptacles 11 and 12 are joined by the cuvette central section 14 which comprises wall sections 15 and 16. These sections are, respectively, extensions of and co-planar with sidewalls 17 and 18 and sidewalls 19 and 20 of the receptacles 11 and 12. Central section 14 also includes a depending cylindrical member 21 which is joined to receptacles 11 and 12 by ribs 22 and 23. Member 21 is provided to be engaged by a locating member of the testing apparatus in which the cuvette is used to align and secure the receptacles 11 and 12 in the light paths of a photo-optical clot detection system.

Looking again at the drawing, it will be observed that cuvette 10 is provided with an aperture 24 at the upper end of sidewall 17 of receptacle 11. This aperture can be detected by a sensing member in the testing apparatus and the samples contained in receptacles 11 and 12 tested accordingly. It will be noted that sidewall 20 of receptacle 12 is provided with an aperture 25 which, in effect, is a "mirror image" of aperture 24. By coding both sides of cuvette 10, the orientation of the cuvette in the test apparatus is immaterial. The sensing device of the test apparatus will detect the identical code regardless of which side of the cuvette is presented to be sensed. This is very evident from FIG. 5 where it is clear that if a cuvette is reversed, the code presented to a sensing device remains the same.

A projection 26 is provided to distinguish receptacle 12 from receptacle 11. Ordinarily it is not necessary to distinguish one receptacle from the other since a sample or specimen from one patient is usually placed in each receptacle of the cuvette. However, if a sample from one patient is placed in receptacle 11 and a sample from a different patient is placed in receptacle 12 it would be necessary to distinguish the receptacles so that the test results could be associated with the proper patient.

Figure 5:
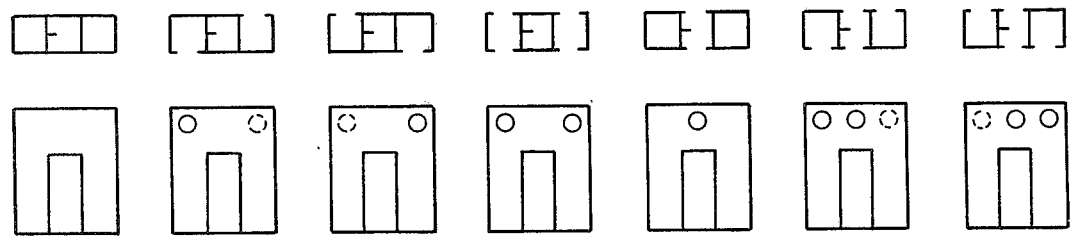
FIG. 5 is a schematic illustration showing various coding arrangements for coding a cuvette.

FIG. 5 illustrates that with a three station code, a cuvette can be coded seven different ways. This means that one of seven different testing procedures can be called for, depending on how a cuvette is coded. A cuvette having an aperture in each of the three code stations could not be differentiated from an absent cuvette. Hence a three aperture code is not used. It is better to have this condition mean that a cuvette is missing and program the testing apparatus accordingly. The cuvettes illustrated in FIG. 5 could be lightly tinted in different colors, each color to correspond to a particular code and testing procedure. Thus, for example, if the cuvette that is coded to call for a prothrombin time test on the samples in both receptacles 11 and 12 is tinted red, the technician would not have to learn the code for that particular testing arrangement. Rather, he would simply select a red tinted cuvette knowing that a red tinted cuvette will be coded to call for a prothrombin test on the samples in each cuvette receptacle. As a further example, when an activated partial thromboplastin test is to be performed on the samples in both cuvette receptacles, that cuvette may be tinted blue. It is to be noted that cuvettes are only lightly tinted so as to not materially affect the transparency of the cuvette, since a light beam is projected through the cuvette in a photo-optical clot detection system.

Having thus described the invention, it is to be understood that other embodiments of the invention, differing from the preferred embodiment described, could be provided without departing from the spirit and scope of the invention. Therefore, it is intended that the foregoing specification and drawing be interpreted as illustrative rather than in a limiting sense.

What is claimed is:

1. A dual cuvette adapted for use in a photometric blood testing apparatus, said cuvette comprising a pair of spaced apart flat sided sample receptacles, connecting means for joining the pair of receptacles to form an integral dual cuvette, said connecting means having a pair of opposite side walls coplanar with the sidewalls of said cuvette receptacles and extending from the top edge of said receptacles downwardly a distance less than the height of a cuvette receptacle and a bottom wall joining the bottom edges of said sidewalls, with a cylindrically shaped locating member depending from said bottom wall and centrally positioned between said pair of sample receptacles by which the cuvette can be mechanically positioned and secured in the testing station of the blood testing apparatus, and machine readable code means being provided on at least one side wall of the cuvette to enable the testing apparatus to sense the code and determine the reagent to be added to and the test to be performed on samples contained in the cuvette receptacles.

2. A dual cuvette according to claim 1 wherein said code means comprises the presence or absence of an aperature in the side wall of said connecting means and the portion of the side walls of the cuvette receptacles aligned therewith.

3. A dual cuvette according to claim 1 or 2 wherein the receptacles are substantially transparent and tinted with a color that corresponds to the machine readable code.

4. A dual cuvette according to claim 1 or 2 wherein identical code means are provided on opposite side walls of the cuvette, whereby the cuvette receptacles and coding are symmetrical about a vertical axis so that one of said code means will be read by a sensing mechanism regardless of the orientation of the cuvette in the testing apparatus.

5. A dual cuvette according to claim 1 or 2 wherein the receptacles are substantially transparent and tinted with a color that corresponds to the machine readable code, and wherein identical code means are provided on opposite side walls of the cuvette, whereby the cuvette is symmetrical and, when placed in the testing apparatus in either of two orientations, will present one of its code means to a code sensing mechanism in the testing apparatus.

6. A dual cuvette according to claim 1 including a rib means extending outwardly from one cuvette receptacle towards the other receptacle and from the top edge of said one cuvette receptacle to the bottom wall of said connecting means, whereby one cuvette receptacle can be differentiated from the other.

7. A dual cuvette according to claim 1 wherein the bottom wall of each receptacle is a flat, thin-walled heat transfer surface, whereby a sample contained in a receptacle can be cooled or heated by a cooling track or a heating track that supports the cuvette as it is transported through the testing apparatus.

* * * * *